(12) United States Patent
Ygartua et al.

(10) Patent No.: US 8,111,384 B2
(45) Date of Patent: Feb. 7, 2012

(54) METHOD FOR MEASURING THERMO-OPTICALLY INDUCED MATERIAL PHASE-CHANGE RESPONSE IN A MULTIPLE LAYER THIN FILM STRUCTURE USING VISIBLE AND ULTRAVIOLET SPECTROSCOPY

(75) Inventors: Carlos L. Ygartua, Palo Alto, CA (US); Lei Zhong, Parker, TX (US); John McCormack, Linlithgow (GB); Robert J. McClelland, San Ramon, CA (US)

(73) Assignee: KLA-Tencor Corporation, Milpitas, CA (US)

( * ) Notice: Subject to any disclaimer, the term of this patent is extended or adjusted under 35 U.S.C. 154(b) by 296 days.

(21) Appl. No.: 12/484,902

(22) Filed: Jun. 15, 2009

(65) Prior Publication Data
US 2010/0318212 A1 Dec. 16, 2010

(51) Int. Cl.
*G01B 11/16* (2006.01)
(52) U.S. Cl. ........... 356/32; 257/2; 257/4; 257/E27.004; 356/301; 700/108

(58) Field of Classification Search .............. 257/2, 4, 257/E29, E27.004, E27.125; 356/301, 32; 700/108
See application file for complete search history.

(56) References Cited

U.S. PATENT DOCUMENTS

| 7,280,184 B2 * | 10/2007 | Hasegawa et al. ............ 355/53 |
| 2007/0181867 A1 * | 8/2007 | Hewak et al. .................... 257/4 |
| 2009/0152664 A1 * | 6/2009 | Klem et al. ............ 257/E31.111 |

\* cited by examiner

*Primary Examiner* — Gregory J Toatley
*Assistant Examiner* — Iyabo S Alli
(74) *Attorney, Agent, or Firm* — Suiter Swantz pc llo

(57) ABSTRACT

A method and device for facilitating measurement of thermo-optically induced material phase change response in a thin planar or a grating film stack is disclosed. The method may include using small-spot visible and ultraviolet spectra (ellipsometric or reflectance) for measuring a material phase change response. The device may include a measurement system platform, at least one electrical resistor, at least one external electric probe, and ohmic contact circuitry.

20 Claims, 6 Drawing Sheets

US 8,111,384 B2

METHOD FOR MEASURING THERMO-OPTICALLY INDUCED MATERIAL PHASE-CHANGE RESPONSE IN A MULTIPLE LAYER THIN FILM STRUCTURE USING VISIBLE AND ULTRAVIOLET SPECTROSCOPY

TECHNICAL FIELD

The present invention generally relates to apparatus and techniques for inspecting a sample, and more particularly to apparatus and techniques for measuring a phase-change in a multiple layer thin film structure.

BACKGROUND

A phase change material may include a substance with a high heat of fusion, which when melted and solidified at a high temperature, is capable of storing and releasing large amounts of energy. Phase change materials may be often used in manufacturing semiconductors and memory, as well as other computer-based applications.

One example of a phase change material may be found in phase-change memory. Phase-change memory may include a type of non-volatile memory that uses the unique behavior of chalcogenide glass, which can be switched between amorphous and crystalline states with the application of heat. The amorphous and crystalline states of the chalcogenide glass have different electrical resistivities and refractive indicies, which may be measured utilizing different means.

SUMMARY

A method and device for facilitating measurement of thermo-optically induced material phase change response in a thin planar or a grating film stack is disclosed. The method may include using small-spot visible and ultraviolet spectra (ellipsometric or reflectance) for measuring a material phase change response and may include the steps of inducing a material phase change with radiant exposure using a pulsed laser, measuring a material phase change response, fitting measured spectra with a spectroscopic model, determining at least one of refractive index dispersion or film layer thickness, and/or correlating a thermo-optically induced change in a refractive index measurement with an electro-thermally induced change in electrical response.

The device for facilitating measurement of thermo-optically induced material phase change response in a thin planar or a grating film stack may include a measurement system platform, at least one electrical resistor, at least one external electric probe, and ohmic contact circuitry.

It is to be understood that both the foregoing general description and the following detailed description are exemplary and explanatory only and are not necessarily restrictive of the invention as claimed. The accompanying drawings, which are incorporated in and constitute a part of the specification, illustrate embodiments of the invention and together with the general description, serve to explain the principles of the invention.

BRIEF DESCRIPTION OF THE DRAWINGS

The numerous advantages of the disclosure may be better understood by those skilled in the art by reference to the accompanying figures in which.

DETAILED DESCRIPTION OF THE INVENTION

Reference will now be made in detail to the subject matter disclosed, which is illustrated in the accompanying drawings.

Figure 1:
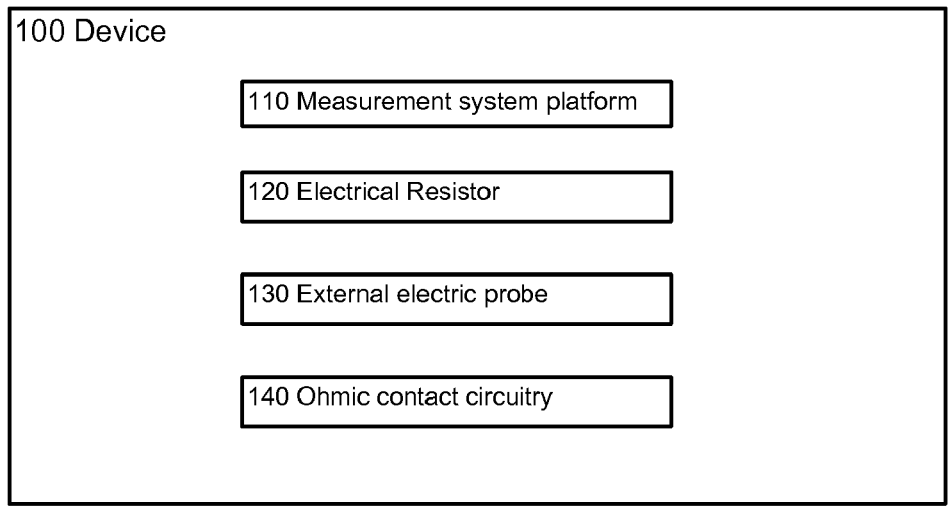
FIG. 1 illustrates an exemplary device for in-line film monitoring in which one or more technologies may be implemented.
Figure 2:
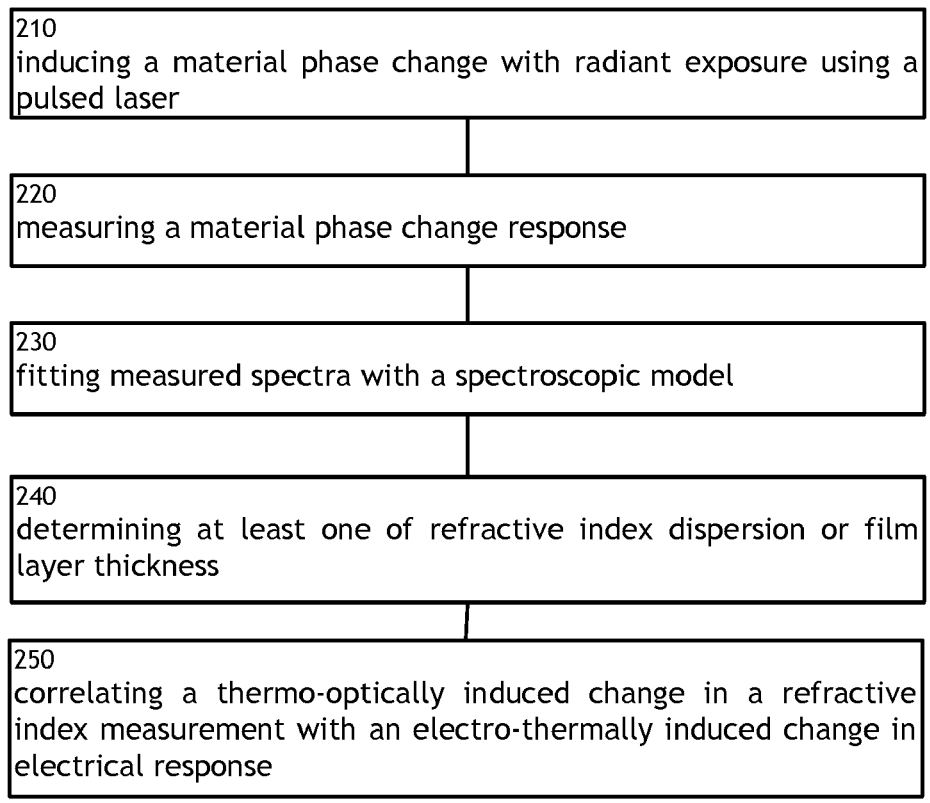
FIG. 2 illustrates a flow diagram illustrating an exemplary method for in-line film monitoring.

Referring generally to FIGS. 1-8, a device 100 and method 200 for facilitating measurement of thermo-optically induced material phase change response in a thin planar or a grating film stack is disclosed. As illustrated in FIG. 1, the device 100 may include a measurement system platform 110, at least one electrical resistor 120, at least one external electric probe 130, and ohmic contact circuitry 140. As illustrated in FIG. 2, the method 200 may include operation 210, operation 220, operation 230, operation 240, and operation 250. The method 200 may include using small-spot visible and ultraviolet spectra (ellipsometric or reflectance) for measuring a material phase change response. The phase change (e.g., from an amorphous phase to a crystalline or mixture of crystalline and amorphous phases) may be induced in the measurement area by radiant exposure with a pulsed laser. Refractive index dispersion (RI) and film layer thickness may be determined by fitting measured spectra with a spectroscopic model. The material phase change response may be characterized by a change in RI and possible change in thickness of the phase change layer(s) in a film stack. The thermo-optically induced change in RI may be correlated with and/or used to predict electro-thermally induced change in electrical response of the phase-change material. A metastable state may be characterized by temporal control of the sequence of radiant (laser) induced phase change and spectroscopic data acquisition.

Operation 210 discloses inducing a material phase change with radiant exposure using a pulsed laser. Operation 220 discloses measuring a material phase change response. Operation 230 discloses fitting measured spectra with a spectroscopic model. Operation 240 discloses determining at least one of refractive index dispersion or film layer thickness. Operation 250 discloses correlating a thermo-optically induced change in a refractive index measurement with an electro-thermally induced change in electrical response.

The electrical measurement of the phase change response may require complete fabrication of the device 100 and/or test structure, which may include the phase change material and/or nearby electrical resistors 120 for providing electro-thermal energy for the phase change. An electrical resistor may include a two terminal electrical component designed to oppose an electrical component and dissipating power. An external electric probe may include connection means to an electrical measurement apparatus. Additionally, the device 100 may include ohmic contact circuitry 140 ("pads") so that external electrical probes 130 may perform the measurement (e.g., resistance vs. applied current). Ohmic contact circuitry may include a region on a semiconductor device that has been prepared so that the current-voltage curve of the device is linear and symmetric. Often, ohmic contact circuitry may include contacts that are sputtered and/or evaporated metal pads that are patterned utilizing photolithography. A measurement system platform may include an apparatus and/or system for making a measurement, such as a KLA-Tencor Aleris™ 8500 and/or a SpectraFx™ system.

One advantage of the optical measurement method is that it may be used to measure the phase change response of the film stack at various stages within the manufacturing process (e.g., as an in-line process monitor). The small spot size (50×50 um for ellipsometric spectra and as small as 2.5×2.5 um for reflectance spectra) and high measurement speed (typically <1 s) may facilitate detailed measurements of process variations. In manufacturing processes, it may be a disadvantage to only have an end-of-line monitor. In general, in-line process monitoring is considered more efficient and cost-effective for process control than end-of-line measurements.

The thin films structures measured may include those used to form integrated circuit (IC) microelectronic devices or may be "test pads" designed to monitor the films in a device. One application of the phase change response measurement is process monitoring of a phase change memory device. Phase change memory cells may currently use chalcogenide glasses, such as $Ge_xSb_yTe_z$, which may undergo reversible phase transformation with exposure to heat. Multiple memory states may also be possible because of the multiple phases that may be thermally induced in these types of materials (e.g., amorphous, face centered cubic, hexagonal close packed, and/or various mixtures).

Figure 3:
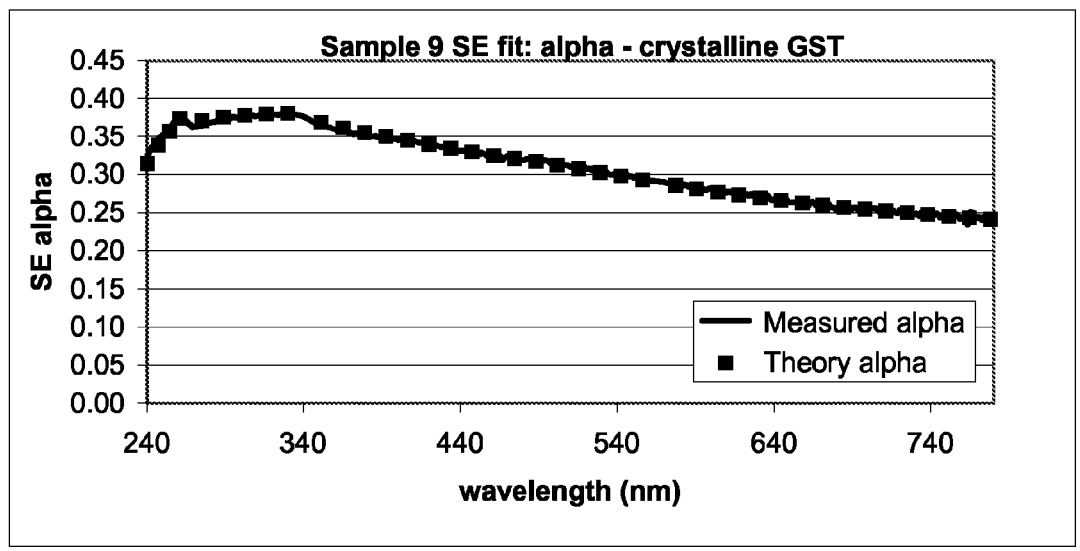
FIG. 3 illustrates an exemplary ellipsometric spectra for $Ge_{22}Sb_{22}Te_{56}$.
Figure 3:
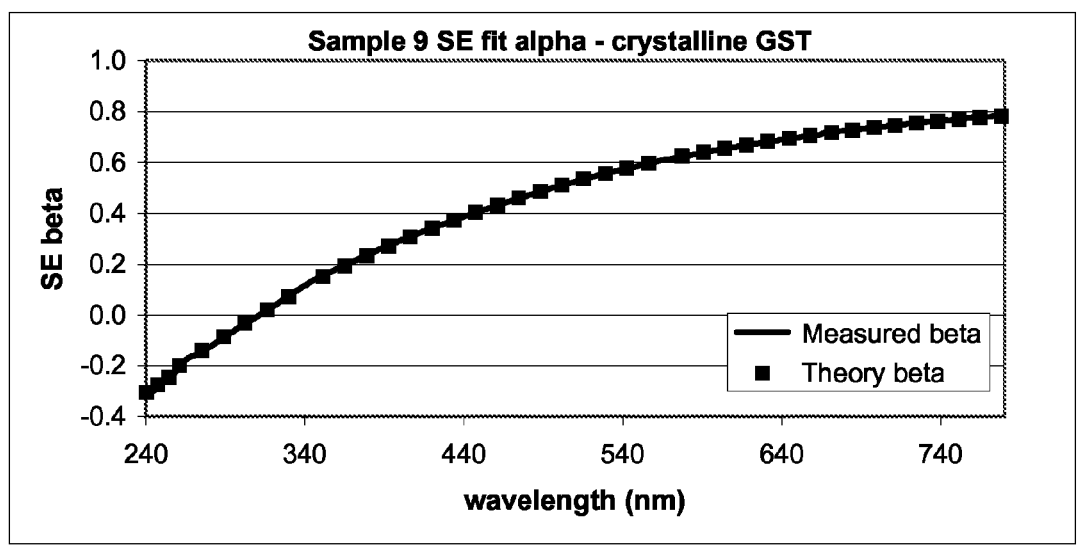
Figure 4:
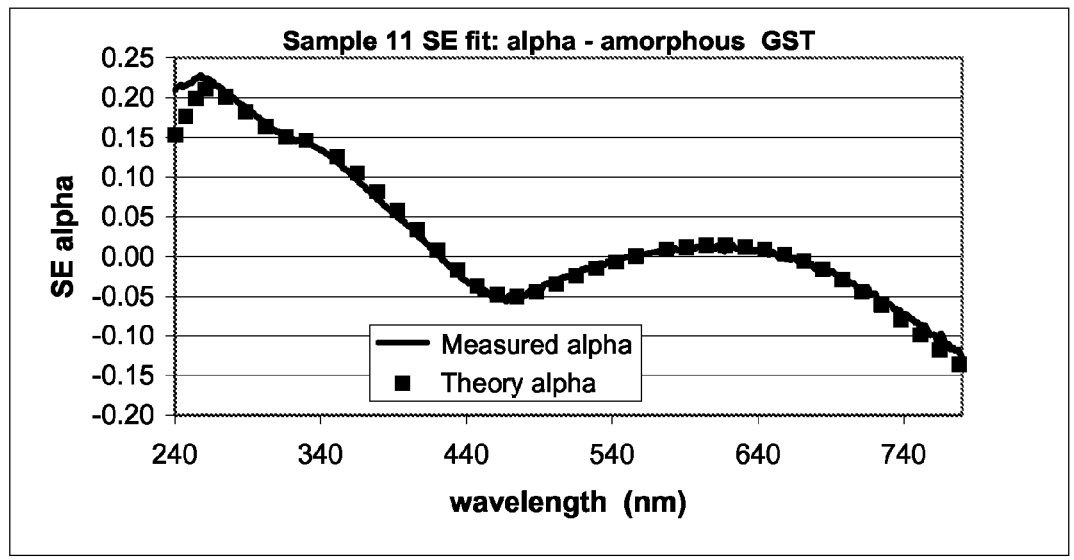
FIG. 4 illustrates an exemplary ellipsometric spectra for $Ge_{22}Sb_{22}Te_{56}$.
Figure 4:
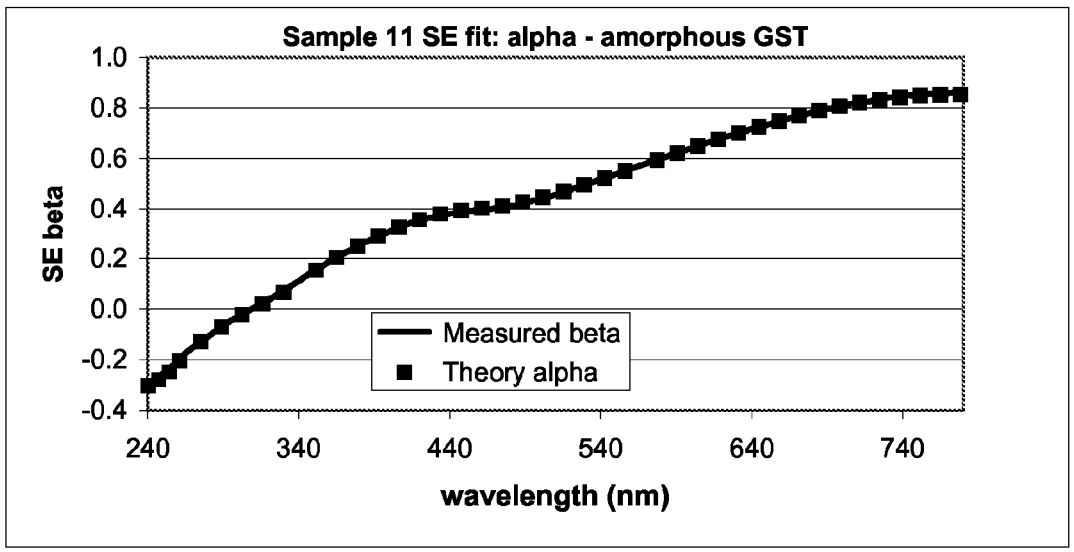
Figures 5, 6:
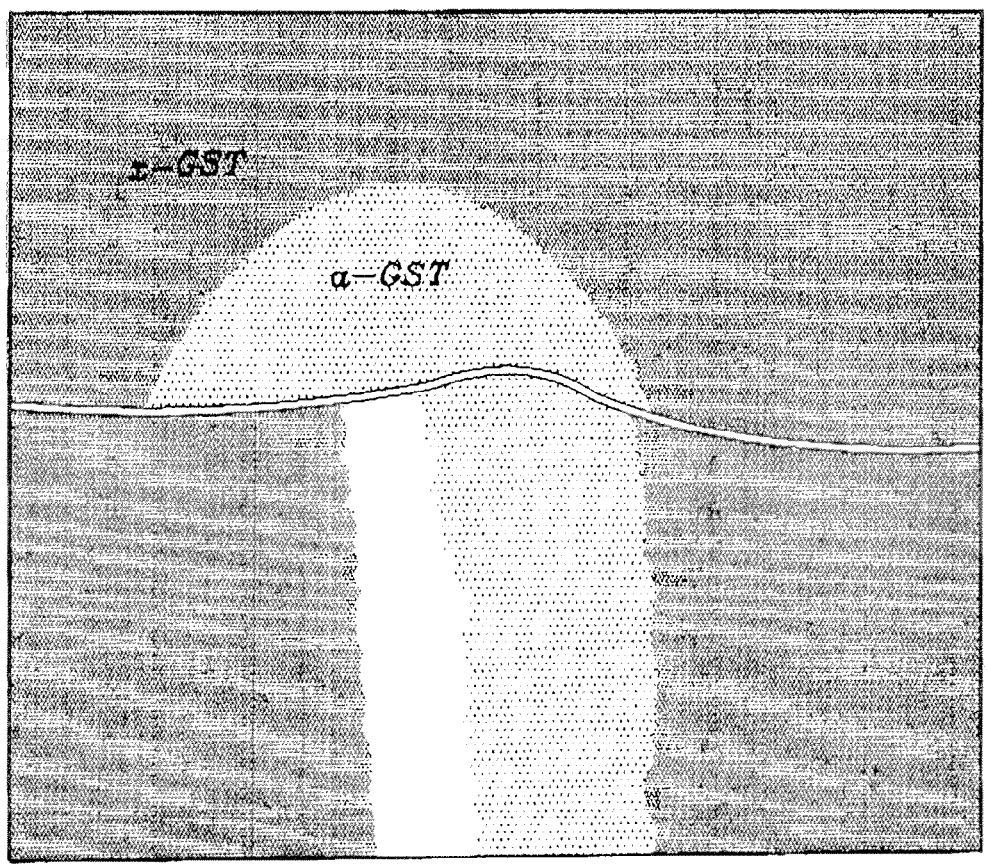
FIG. 5 illustrates an exemplary chart depicting a film stack model used in an approximation program.
FIG. 6 illustrates an exemplary image of a memory cell.
Figure 7:
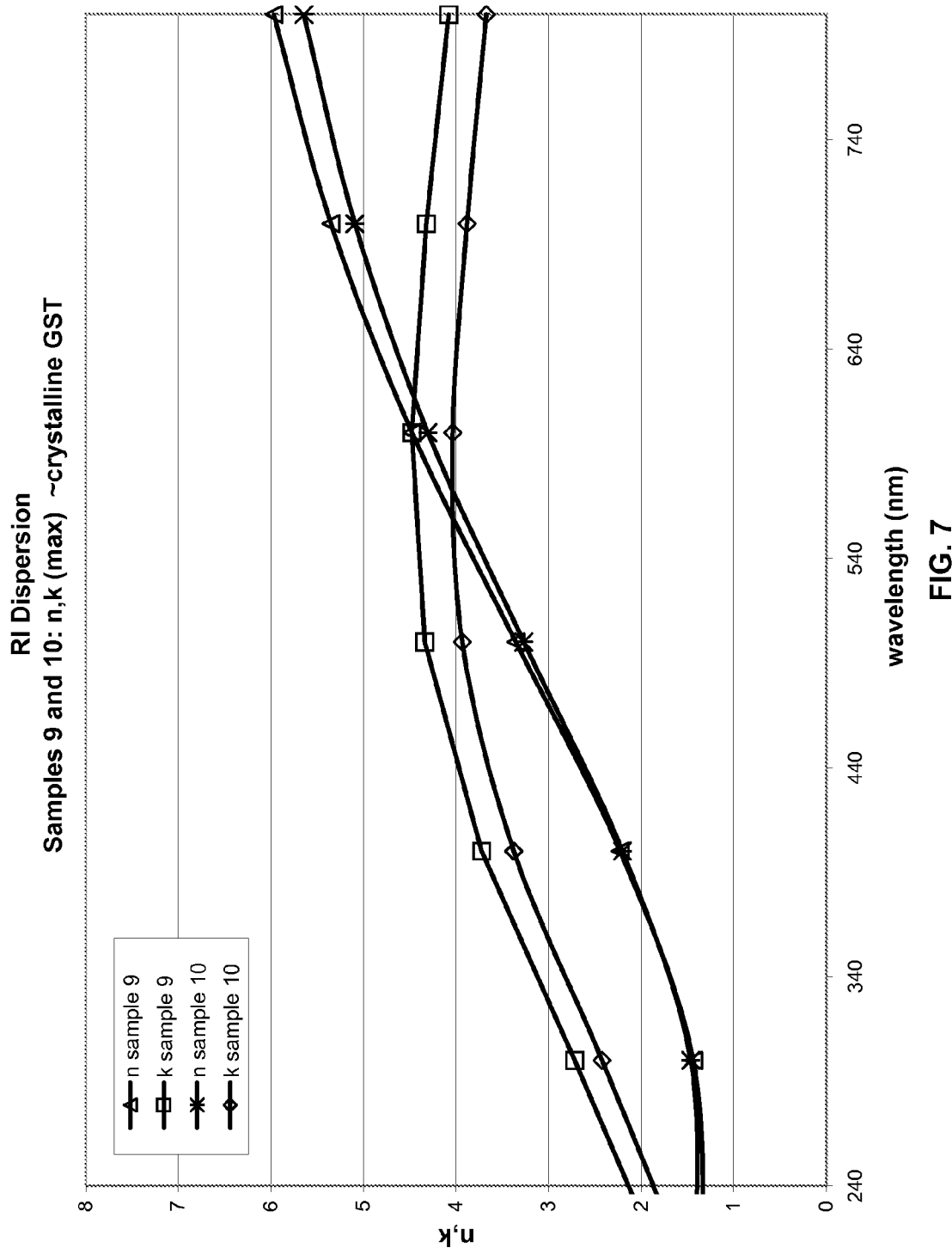
FIG. 7 illustrates an exemplary refractive index (RI) dispersion of crystalline $Ge_{22}Sb_{22}Te_{56}$.
Figure 8:
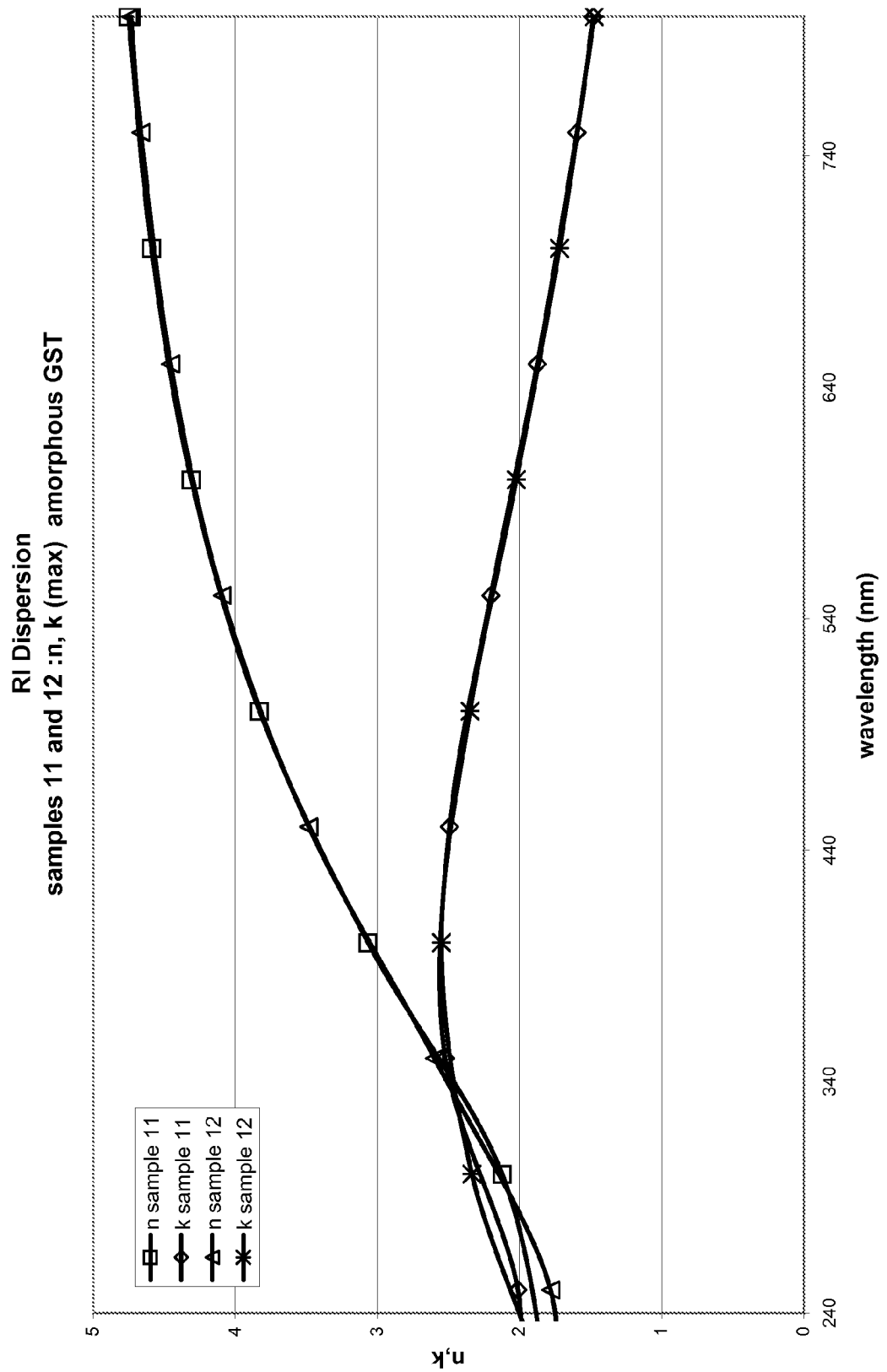
FIG. 8 illustrates an exemplary refractive index (RI) dispersion of amorphous $Ge_{22}Sb_{22}Te_{56}$.

The measurement process may include radiant exposure with a pulsed laser at a specified wavelength with a pulse of a specified power and duration, subsequent measurement of the spectra, and fitting of the spectroscopic model to the measured spectra. Some examples of a fitted spectroscopic model to measured spectra for $Ge_{22}Sb_{22}Te_{56}$ are illustrated in FIGS. 3-4. For example, FIG. 3 illustrates an ellipsometric spectra fit for 433 Å crystalline $Ge_{22}Sb_{22}Te_{56}$ on 4055 Å $SiO_2$ on Si. FIG. 4 illustrates an ellipsometric spectra fit for 490 Å amorphous $Ge_{22}Sb_{22}Te_{56}$ on 3925 Å SiO2 on Si. The spectroscopic model may include a RI model for the phase change material, the substrate, and possibly other film layers. The spectroscopic model may also include a measurement of surface roughness ("haze level") by a scattering parameter and/or by a thin film approximation for the surface roughness (e.g., an effective medium of oxide and air). In addition, the spectroscopic model may include a patterned film structure that comprises a one or two dimensional grating. An example of a film stack model user interface is illustrated in FIG. 5. The film stack model illustrated in FIG. 5 includes an oxide on $Ge_{22}Sb_{22}Te_{56}$ on a $SiO_2$/Si substrate. FIG. 6 illustrates a scanning electron microscope image of an operational $Ge_{22}Sb_{22}Te_{56}$ memory cell. In FIG. 6, a heater in the cell (the dark vertical line) may heat the phase-change material for changing the phase. Surface scattering may be accounted for via a roughness parameter. The $Ge_{22}Sb_{22}Te_{56}$ RI in this example is modeled with a BEMA (Bruggeman Effective Medium Approximation) with RI components for crystalline and amorphous $Ge_{22}Sb_{22}Te_{56}$. Some examples of the RI are shown in FIGS. 7-8. FIG. 7 illustrates an RI dispersion of crystalline $Ge_{22}Sb_{22}Te_{56}$, while FIG. 8 illustrates an RI dispersion of amorphous (as deposited) $Ge_{22}Sb_{22}Te_{56}$.

Surface roughness or haze level may be an important indicator of the structural state of the material. For example, a material (e.g., $Ge_{22}Sb_{22}Te_{56}$) surface may be smooth in the (single) crystalline and amorphous phases, but may be rough in the intermediate phase because of multiple crystalline phases.

At least some parameters to be measured may be specified in a measurement "recipe." The recipe may determine the manner in which spectroscopic model parameters may be varied to fit the measured spectra via a regression algorithm known to those in the art. The recipe may report measured parameters, for example, layer thickness, RI at specified wavelengths, RI model parameters, etc. An important function of the recipe may include minimization of measurement correlation between parameters. This may be accomplished by taking into account the sensitivity of the measured parameters to wavelength range. Thickness and RI parameters may be individually optimized in different stages of the regression process with different wavelength ranges or measurement sub-systems (e.g., ellipsometric visible +UV, ellipsometric DUV, UV or visible reflectance, and/or single wavelength ellipsometry). For the phase change materials, the RI model may be constructed such that the RI model parameters correlate with the different phases of the material. For example, predetermined RI sets may be utilized by a RI lookup model with an RI lookup parameter defined by a particular phase of the material.

The measurement recipe may also control the sequence of measurement spot exposure to the laser (for inducing the phase change) and subsequent spectroscopic exposure (data acquisition). The power and duration of the laser exposure may be adjusted to achieve the targeted phase of the material. The spectroscopic exposure (wavelength range and time) may also be specified thereby providing means of minimizing the effects (e.g., electronic band saturation) of exposure from the measurement itself.

The proposed method may be implemented with existing spectroscopic measurement systems platforms, such as the KLA-Tencor Aleris 8500, as an integrated metrology solution for in-line monitoring of phase change materials and devices. The combination of inducing phase change and measuring the optical properties and/or layer thickness in one system may provide unique and novel process control capability. In one example, RI models, based on the Lorentz oscillator approximation, have been developed for amorphous and crystalline $Ge_{22}Sb_{22}Te_{56}$ using 240-800 nm ellipsometric and reflectance spectra from a planar film stack of $Ge_{22}Sb_{22}Te_{56}$ on $SiO_2$ on a Si substrate. Spectra were measured (using a KLA-Tencor Aleris 8500) on samples with nominally 450 Å of $Ge_{22}Sb_{22}Te_{56}$.

In the present disclosure, the methods disclosed may be implemented as sets of instructions or software readable by a device. Further, it is understood that the specific order or hierarchy of steps in the methods disclosed are examples of exemplary approaches. Based upon design preferences, it is understood that the specific order or hierarchy of steps in the method can be rearranged while remaining within the disclosed subject matter. The accompanying method claims present elements of the various steps in a sample order, and are not necessarily meant to be limited to the specific order or hierarchy presented.

It is believed that the present disclosure and many of its attendant advantages will be understood by the foregoing description, and it will be apparent that various changes may be made in the form, construction and arrangement of the components without departing from the disclosed subject matter or without sacrificing all of its material advantages. The form described is merely explanatory, and it is the intention of the following claims to encompass and include such changes.

What is claimed is:

1. A method for in-line film monitoring, comprising:
   inducing a material phase change with radiant exposure using a pulsed laser;
   measuring a material phase change response;
   fitting measured spectra with a spectroscopic model;
   determining at least one of refractive index dispersion or film layer thickness; and
   correlating a thermo-optically induced change in a refractive index measurement with an electro-thermally induced change in electrical response.

2. The method in claim 1, wherein the inducing a material phase change with radiant exposure using a pulsed laser comprises:
   inducing an amorphous phase to crystalline phase change.

3. The method in claim 1, wherein the inducing a material phase change with radiant exposure using a pulsed laser comprises:
   inducing a material phase change in a chalcogenide glass.

4. The method in claim 3, wherein the inducing a material phase change in a chalcogenide glass comprises:
   inducing a material phase change in $Ge_{22}Sb_{22}Te_{56}$.

5. The method in claim 1, wherein the inducing a material phase change with radiant exposure using a pulsed laser comprises:
   controlling a sequence of measurement spot exposure to the pulsed laser.

6. The method in claim 1, wherein the inducing a material phase change with radiant exposure using a pulsed laser comprises:
   adjusting at least one of power and time duration of the pulsed laser.

7. The method in claim 1, wherein the inducing a material phase change with radiant exposure using a pulsed laser comprises:
   specifying at least one of a wavelength or time duration of a spectroscopic exposure.

8. The method in claim 1, wherein the measuring a material phase change response comprises:
   measuring a change in refractive index (RI).

9. The method in claim 8, wherein the measuring a change in refractive index (RI) comprises:
   measuring a change in refractive index (RI) at a specified wavelength.

10. The method in claim 8, wherein the measuring a change in refractive index (RI) comprises:
    measuring refractive index (RI) model parameters.

11. The method in claim 1, wherein the measuring a change in refractive index (RI) comprises:
    specifying a structural state.

12. The method in claim 1, wherein the fitting measured spectra with a spectroscopic model comprises:
    utilizing a regression algorithm.

13. The method in claim 1, wherein the fitting measured spectra with a spectroscopic model comprises:
    fitting measured spectra with a spectroscopic model including a refractive index (RI) model for a phase change material.

14. The method in claim 13, wherein the fitting measured spectra with a spectroscopic model including a refractive index (RI) model for a phase change material comprises:
    fitting measured spectra with a spectroscopic model including a refractive index (RI) model for layers other than the phase change material.

15. The method in claim 1, wherein the fitting measured spectra with a spectroscopic model comprises:
    fitting measured spectra with at least one of surface roughness measurement or haze level.

16. The method in claim 1, wherein the fitting measured spectra with a spectroscopic model comprises:
    fitting measured spectra with a spectroscopic model including at least one patterned film structure having at least one of a one dimensional grating or a two dimensional grating.

17. A device for in-line film monitoring, comprising:
    a measurement system platform configured to measure a phase change material;
    at least one electrical resistor configured to provide electro-thermal energy for inducing a phase change in the phase change material;
    at least one external electric probe configured to measure the phase change material; and
    ohmic contact circuitry configured to couple with the at least one external probe.

18. The device in claim 17, wherein the measurement system platform configured to measure a phase change material comprises:
    a measurement system platform configured to measure a chalcogenide glass.

19. The device in claim 18, wherein the measurement system platform configured to measure a chalcogenide glass comprises:
    a measurement system platform configured to measure Ge22Sb22Te56.

20. The device in claim 17, wherein the measurement system platform configured to measure a phase change material comprises:
    a measurement system platform configured to measure a phase change material during a manufacturing process of a thin film structure.

* * * * *